US00PP19257P3

(12) United States Plant Patent
Stevenson

(10) Patent No.: US PP19,257 P3
(45) Date of Patent: Sep. 23, 2008

(54) ***COROKIA* PLANT NAMED 'PHANTOM'**

(50) Latin Name: *Corokia virgata*
Varietal Denomination: Phantom

(76) Inventor: John Stevenson, P.O. Box 8428, Symonds Street, Auckland (NZ)

( * ) Notice: Subject to any disclaimer, the term of this patent is extended or adjusted under 35 U.S.C. 154(b) by 0 days.

(21) Appl. No.: 11/975,600

(22) Filed: Oct. 20, 2007

(65) Prior Publication Data

US 2008/0134385 P1 Jun. 5, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para

(57) ABSTRACT

A new cultivar of *Corokia* plant named 'Phantom' that is characterized by narrow leaves that are colored dark brown on the upper surface and vigorous growth.

1 Drawing Sheet

Botanical Classification: *Corokia virgata*. Variety Denomination: 'Phantom'.

BACKGROUND OF THE INVENTION

The present invention relates to a new and distinct cultivar of *Corokia* plant botanically known as *Corokia virgata* and hereinafter referred to by the cultivar name 'Phantom'.

The new cultivar originated from a cross of the male or pollen parent plant an unidentified cultivar of *Corokia virgata* and the female or seed parent plant an unidentified cultivar of *Corokia virgata*. 'Phantom' was selected as a single plant from the progeny of the stated cross by the inventor in a cultivated area of Auckland, New Zealand in 2004.

Asexual reproduction by terminal cuttings of the new cultivar 'Phantom' was first performed in 2004 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Corokia* cultivar 'Phantom'.

1. *Corokia* 'Phantom' exhibits leaves that are colored dark brown on the upper surface.
2. *Corokia* 'Phantom' exhibits vigorous growth.
3. *Corokia* 'Phantom' exhibits narrow leaves.

The closest comparison cultivar is *Corokia* 'Frosted Chocolate'.

The new cultivar 'Phantom' is distinguishable from 'Frosted Chocolate' unpatented by the following characteristics:

1. 'Phantom' has leaves that are brown on the upper side. The upper leaves of 'Frosted Chocolate' are grey-orange.
2. 'Phantom' has narrower leaves than the leaves of 'Frosted Chocolate'.
3. 'Phantom' has shorter leaves than the leaves of 'Frosted Chocolate'.
4. 'Phantom' has a longer internode length.

The new cultivar 'Phantom' is distinguishable from the parent plants by the following characteristics:

1. 'Phantom' has leaves that are brown on the upper side. The upper leaves of the parent plants are green.
2. 'Phantom' has narrower leaves.
3. 'Phantom' has shorter leaves.
4. 'Phantom' has a longer internode length.

BRIEF DESCRIPTION OF THE DRAWING

The accompanying photograph illustrates the distinguishing traits of *Corokia* 'Phantom'. The plant in the photograph shows an overall view of a 1 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Corokia* cultivar named 'Phantom'. Data was collected in Auckland, New Zealand from 1 year old plants grown outdoors in 3.3 liter containers. The time of year was Winter in the Southern Hemisphere and the temperature range was 12 to 18 degrees Centigrade during the day and 4 to 11 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Phantom' has not been tested under all possible conditions and phenotypic differences may be observed with variations in environmental, climatic, and cultural conditions, however, without any variance in genotype.

Botanical classification: *Corokia virgata* 'Phantom'.
Use: Ornamental perennial shrub.
Vigor: Vigorous.
Growth rate: 0.6 m per year.
Growth habit: Upright.
Plant shape: Narrowly conical.
Suitable container size: 2 L.

Height: Average 2 m in height.
Width: Average 1.6 m in width.
Low temperature tolerance: −12° Centigrade.
High temperature tolerance: 28° Centigrade.
Propagation: Terminal cuttings.
Time to initiate roots in summer: 40 days at 22° C.
Time to initiate roots in winter: 40 days at 22° C.
Time to produce a rooted cutting or liner in summer: 90–120 days at 18°–24° C.
Time to produce a rooted cutting or liner in winter: 90–120 days at 10°–15° C.
Root system: Fine and fibrous.
Lateral Branches:
*Quantity.*—2.
*Pinching.*—Pinch at third set of leaves.
*Lateral branch length.*—220 mm.
*Lateral branch diameter.*—1.5 mm.
*Internode length.*—30 mm.
*Stem shape.*—Rounded.
*Stem aspect.*—Upright.
*Stem strength.*—Strong.
*Stem color.*—200A with webbed pubescence 196C.
*Pubescence.*—Colored 196C.
Foliage:
*Texture.*—Leathery.
*Quantity of leaves per branch.*—Approximately 12.
*Leaf arrangement.*—Scattered.
*Compound or single.*—Single.
*Leaf shape.*—Oblanceolate.
*Leaf apex.*—Acute.
*Leaf base.*—Attenuate.
*Leaf length.*—Average 20 mm in length.
*Leaf width.*—Average 6 mm in width.
*Pubescence.*—Present on the bottom side.
*Leaf margin.*—Entire.
*Young leaf color* (*upper surface*).—200B.
*Young leaf color* (*lower surface*).—196D.
*Mature leaf color* (*upper surface*).—200B.
*Mature leaf color* (*lower surface*).—196D.
*Durability of foliage to stress.*—Good.
Petiole:
*Petiole length.*—1 mm.
*Petiole diameter.*—0.5 mm.
*Petiole color.*—196D.
Flowers: Flowers have not been observed.
Disease and insect resistance: Plants of the new *Corokia* have not been observed for disease or insect resistance.

It is claimed:

1. A new and distinct variety of *Corokia* plant named 'Phantom' as described and illustrated.

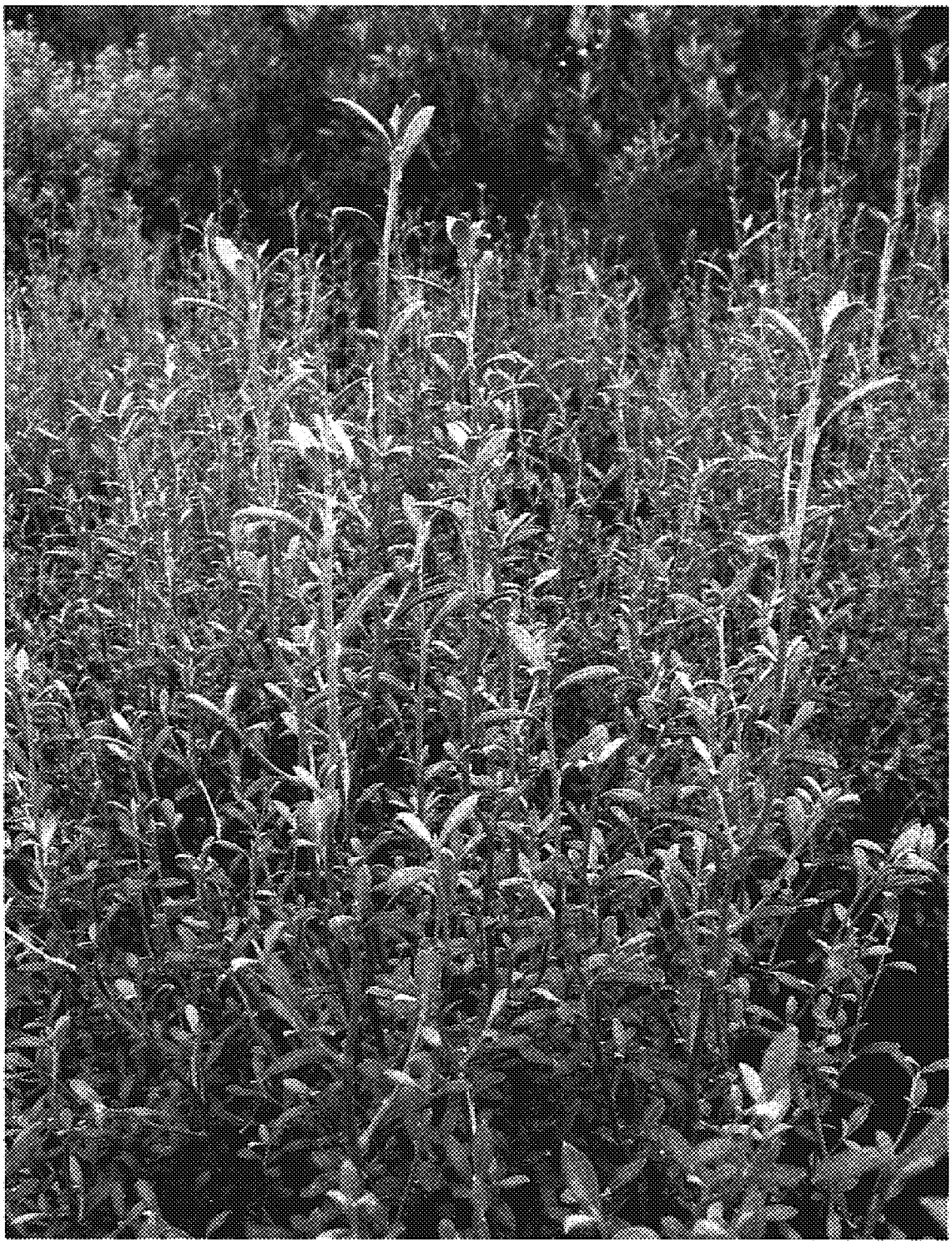

* * * * *